United States Patent [19]

Hopkins, Jr. et al.

[11] Patent Number: 5,362,766
[45] Date of Patent: Nov. 8, 1994

[54] METHOD FOR IMMOBILIZING SUPERABSORBENT POLYMERS BY HOMOGENIZATION OF A SUSPENSION OF SAME

[75] Inventors: John B. Hopkins, Jr., Pineville; Joanne C. Maheras, Charlotte, both of N.C.; John B. Morton, Blacksburg, Va.

[73] Assignee: Hoechst Celanese Corporation, Somerville, N.J.

[21] Appl. No.: 28,503

[22] Filed: Mar. 9, 1993

[51] Int. Cl.⁵ .................... C08J 9/28; A61L 15/22
[52] U.S. Cl. .................... 523/105; 424/443; 428/265
[58] Field of Search ............ 523/105; 424/443; 428/265

[56] References Cited

U.S. PATENT DOCUMENTS

| | | | |
|---|---|---|---|
| 2,362,182 | 12/1941 | Baker | 106/183 |
| 3,669,103 | 6/1972 | Harper et al. | 128/156 |
| 4,076,663 | 2/1978 | Masuda et al. | 260/17.4 |
| 4,115,332 | 9/1978 | Young et al. | 260/17.4 |
| 4,133,784 | 1/1979 | Otey et al. | 260/17.4 |
| 4,197,371 | 4/1980 | Horst et al. | 521/84 |
| 4,200,558 | 4/1980 | Holst et al. | 260/17 A |
| 4,286,082 | 8/1981 | Tsubakimoto et al. | 526/240 |
| 4,337,181 | 6/1982 | Otey et al. | 523/128 |
| 4,454,268 | 6/1984 | Otey et al. | 524/47 |
| 4,560,372 | 12/1985 | Pieniak | 604/369 |
| 4,676,784 | 6/1987 | Erdman et al. | 604/368 |
| 4,724,114 | 2/1988 | McFarland et al. | 264/511 |
| 4,914,170 | 4/1990 | Chang et al. | 526/240 |
| 4,990,541 | 2/1991 | Nielsen et al. | 521/70 |
| 5,079,080 | 1/1992 | Schwarz | 428/288 |
| 5,087,513 | 2/1992 | Kim | 428/283 |

FOREIGN PATENT DOCUMENTS

| | | |
|---|---|---|
| 0359615 | 3/1990 | European Pat. Off. . |
| 0425269 | 2/1991 | European Pat. Off. . |
| 2930191 | 2/1980 | Germany . |
| 57-92032 | 6/1982 | Japan . |
| 1034296 | 6/1966 | United Kingdom . |

OTHER PUBLICATIONS

07/805,538, Dec. 11, 1991, Method For Immobilizing Superabsorbent Polymer and Products Derived Therefrom.

Primary Examiner—G. S. Kishore
Assistant Examiner—Peter F. Kulkosky
Attorney, Agent, or Firm—R. H. Hammer, III

[57] ABSTRACT

A method for the manufacture of an absorbent material containing a superabsorbent polymer is disclosed herein. The processing steps include: providing a matrix material in a suitable solvent; mixing particles of a superabsorbent polymer into said solutioned matrix material to form a suspension; homogenizing the suspension; and removing the solvent from the suspension.

4 Claims, No Drawings

METHOD FOR IMMOBILIZING SUPERABSORBENT POLYMERS BY HOMOGENIZATION OF A SUSPENSION OF SAME

FIELD OF THE INVENTION

This invention is directed to a method for making a material comprised of a superabsorbent polymer immobilized in a matrix material. This method utilizies a homogenizer.

BACKGROUND OF THE INVENTION

In U.S. patent application Ser. No. 07/805,538 filed Dec. 11, 1991 and which is incorporated herein by reference, there is described a new material comprising a combination of a superabsorbent polymer (SAP) and a matrix material. The material has good absorbent and retention properties and immobilizies the SAP. The described process requires that a suspension of SAP and matrix material be cooled prior to formation of the final product. The process, however, involves the use of an energy intensive step, the cooling step. Accordingly, further work has been done on the manufacturing process for this material. That work has been directed to the elimination of this costly cooling step.

SUMMARY OF THE INVENTION

A method for the manufacture of an absorbent material containing a superabsorbent polymer is disclosed herein. The processing steps include: providing a matrix material in a suitable solvent; mixing particles of a superabsorbent polymer into said solutioned matrix material to form a suspension; homogenizing the suspension; and removing the solvent from the suspension.

DETAILED DESCRIPTION OF THE INVENTION

The terms "superabsorbent polymer" or "SAP", as used herein, refer to any conventional superabsorbent polymer, as that term is commonly applied in the art. Examples of such SAPs are polymers of water soluble acrylic or vinyl monomers that are cross-linked with a polyfunctional reactant. Also included are starch modified polyacrylic acids and hydrolyzed polyacrylonitrile and their alkali metal salts. A more through recitation of SAPs is presented in U.S. Pat. No. 4,990,541, which is incorporated herein by reference.

A number of such SAPs are commercially available and these are also suitable for use in the present invention. A preferred superabsorbent polymer is commercially available under the tradename SANWET®, a starched modified superabsorbent polymer, from Hoechst Celanese Corporation, Charlotte, N.C. Sanwet® is a starched grafted polyacrylate sodium salt that has the capacity to absorb as much as 800 times its own weight in liquid. Other commercially available SAPs include: DRYTECH® 520 SUPERABSORBENT POLYMER available from Dow Chemical Company, Midland Mich. (Drytech® is a superabsorbent derived from polypropenoic acid); AQUA KEEP manufactured by Seitetsu Kagaku Co., Ltd.; ARASORB manufactured by Arakawa Chemical (U.S.A.) Inc.; ARIDALL 1125 manufactured by Chemdall Corporation; and FAVOR manufactured by Stockhausen Inc.

The term "matrix material" as used herein, refers to a material, when cast or extruded, hardens into a non-expanded solid. A non-expanded solid is a compressed, or substantially continuous, hardened material. Thus, a non-expanded solid is a material that does not exhibit a visually discernable expanded structural network, e.g. the cellular structure of a foam. By a hardened, solid material is meant that it is not a fluid. Despite being characterized as a hardened solid, these materials can be made to be very pliable and flexible. Additionally, the materials can be made porous as would be desirable for filtration membranes.

Non-limiting examples of suitable matrix materials include: 1) cellulose esters (e.g., cellulose acetate, cellulose diacetate, and cellulose triacetate, cellulose propionate, cellulose butyrate) and mixtures thereof; 2) polymers of acrylic acid esters (e.g. polymethyl methacrylate and polyethyl methacrylate); and 3) polyvinyl esters (e.g. polyvinyl acetate). Suitable matrix materials further comprise copolymers and combinations of the forementioned materials.

The matrix material may further comprise additives to enhance the physicochemical characteristics of the composition and the resulting product. Such additives include conventional plasticizers known to those skilled in the art. Examples of such plasticizers are phthalate esters (e.g., diethyl phthalate and dimethyl phthalate), phosphate esters, low molecular weight polymers (e.g., polypropylene glycol), oleates, sebacates, adipates, sulfonamides, and glycol derivatives (e.g., glycerin and triacetin).

The term "suspension", is used herein, refers to a mixture containing a substantially uniform distribution of solute and particulate matter throughout the liquid carrier.

The term "solvent" refers to any suitable solvent for the matrix materials set forth above. Such solvents are well known to those of ordinary skill in the art. Examples of the solvents include volatile aqueous liquid such as low molecular weight aldehydes and ketones, hydrocarbons and halogenated hydrocarbons, esters and ethers. Specific examples of these solvents expressly capable of solutioning cellulose esters are disclosed in U.S. Pat. No. 2,362,182, which is incorporated herein by reference. Those solvents include: acetone, methyl ethyl ketone, methyl acetate, ethyl acetate, propyl acetate, methyl formate, ethyl formate, propyl formate, and combinations thereof. Other suitable solvents are: acetic acid, methylene chloride, methanol, and combinations thereof. Especially preferred solvents are acetone, methylene chloride, methanol, and combinations there.

The term "mixing", as used herein, refers to any unit operation sufficient to wet the particles of SAP with the solutioned matrix material. For example, a high speed, high shear mixer, such as those available from Jaygo, Inc. of Mahwah, N.J., maybe used.

The term "homogenzing", as used herein refers to the unit operation whereby the blending or emulsification of a substance is caused by, for example, forcing the substance through a fine opening and then against a hard surface. For example, such units are available from Microfluidics Corporation, Newton, Mass. Two units are Microfluidics' HC-2000 Sanitary Homogenizer and M-110F microfluidizer.

The following examples further illustrate the invention. They are presented solely for the purpose of illustration and should not be interpreted as being limitations on the invention.

The absorbency and retention tests discussed below are outlined after the examples.

EXAMPLE 1

2322.6 grams of a dope solution of cellulose acetate-/acetone (% solids=0.268, cellulose acetate is Hoechst Celanese's Flake product HB 105), 622.5 grams of Sanwet ® IM-1000, 2490.0 grams of acetone, and 249.0 grams glycerine are added to a 2 gallon high shear mixer (Jaygo, Inc.) and are mixed (at 580 RPM) for one hour. This mixture was then run through (single pass) a homogenizer at 1800 PSIG. The homogenizer was a Microfluidics Corporation, Newton Mass., Model No. HC2000. The homogenized mixture was cold cast into a film by means of a film caster. The films were air dried and then tested for absorbency and retention of a 0.9% saline solution and compared to the materials produced by the procedure set forth in U.S. patent application Ser. No. 07/805,538 filed Dec. 11, 1991. The results of those tests are set forth below in Table 1, the present invention is denoted as "1" and the comparison material is denoted as "C".

TABLE 1

|  | 1 | C |
|---|---|---|
| Absorption g/g | 29.2 | 22.2 |
| Retention g/g | 17.3 | 19.2 |

EXAMPLE 2

The procedure according to Example 1 was repeated, using a F Microfluidics model with the operating pressure varied from 2,000 psi to 10,000 psi. The temperature and pressure of the mixture supplied to the homogenizer were 35° C. and 60 psi. These samples were tested for absorbency and retention and the results are set forth below in Table 2.

TABLE 2

| Pressure (psig) | THRU-PUT (g/min) | ABSORBENCY (g/g) 0.9% Saline | RETENTION (g/g) 0.9% Saline |
|---|---|---|---|
| 2,000 | 161 | 19.3 | 15.6 |
| 6,000 | 416 | 19.4 | 14.8 |
| 10,000 | 522 | 18.0 | 15.5 |

Analytical Test Method Determination of Total Absorbency and Centrifuge Retention The analytical procedure whereby absorbency and retention are measured follows:

Summary: The superabsorptive material ("SAM") is weighted dry and placed in a nylon bag. The nylon bag is placed in the fluid to be absorbed and weight gain is a measure of the absorptive capacity. The nylon bag is then placed in a special basket and centrifuged for a specified period of time (see below) to determine the amount of fluid retained.

Reagents Required: Saline solution (0.900±0.005 wt/wt % aqueous NaCl solution) or Citrated (anticoagulant) certified disease-free animal blood.

Equipment and Materials Required:
1. Balance, accurate to the nearest 0.001 g.
2. Weighing boats or weighing paper.
3. 200 mesh nylon heat-sealable cloth stock or equivalent.
4. Timer, 30 minute minimum capacity.
5. Plastic pan, approximately 15"×20"×5" deep to hold test fluid.
6. Drying rack or line with clips.
7. Heat Sealer, Vertrod Model 9A, 9A-CAB or equivalent.
8. Deluxe Dynac II Centrifuge (Fisher Catalog No. 05-100-26) or equivalent.
9. Centrifuge retention basket.

The present invention maybe embodied in other specific forms without departing from the spirit or essential attributes thereof and, accordingly, reference should be made to the appended claims, rather than to the foregoing specification, as indicating the scope of the invention.

We claim:

1. A process for making a material containing a superabsorbent polymer comprising the steps of:
   providing a matrix material in a suitable solvent, the matrix material being selected from the group consisting of cellulose esters, acrylic acid esters, polyvinyl esters, copolymers of the foregoing and combinations thereof;
   mixing particles of a superabsorbent polymer into said solutioned matrix material to form a suspension;
   homogenizing the suspension at a pressure greater than 2000 psig; and
   removing the solvent from the suspension.

2. The process of claim 1 wherein the suspension is formed by mixing the composition at high shear for at least about one hour.

3. The process of claim 1 wherein the matrix material is selected from the group consisting of cellulose acetate, cellulose triacetate, cellulose triacetate, cellulose propionate, cellulose butyrate, and mixtures thereof.

4. The process of claim 1 wherein the suitable solvent is selected from the group consisting of acetone, methyl ethyl ketone, methyl acetate, ethyl acetate, propyl acetate, methyl formate, ethyl formate, propyl formate, methylene chloride, methanol, and combinations thereof.

* * * * *